US00PP28448P3

(12) United States Plant Patent
Werner

(10) Patent No.: US PP28,448 P3
(45) Date of Patent: Sep. 26, 2017

(54) ***BUDDLEJA* PLANT NAMED 'MISS VIOLET'**

(50) Latin Name: ***Buddleja davidii, lindleyana,* and *globosa***
Varietal Denomination: Miss Violet

(71) Applicant: Dennis James Werner, Raleigh, NC (US)

(72) Inventor: Dennis James Werner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 135 days.

(21) Appl. No.: 14/545,797

(22) Filed: Jun. 18, 2015

(65) Prior Publication Data

US 2016/0374243 P1 Dec. 22, 2016

(51) Int. Cl.
*A01H 5/00* (2006.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct variety of *Buddleja* plant named 'Miss Violet' substantially as illustrated and described, characterized by its compact stature, dense and semi-upright growth habit, oblong-elliptic leaf shape, violet flower color, distorted male flower parts (anthers) resulting in male sterility, and female structures that show reduced function, resulting in reduced seed formation.

4 Drawing Sheets

Latin name of the genus and species: Genus: *Buddleja*. Species: complex hybrid including *davidii, lindleyana*, and *globosa*.

Variety denomination: The inventive cultivar of *Buddleja* disclosed herein has been given the variety denomination 'Miss Violet'.

RELATED APPLICATION INFORMATION

This application claims priority under 35 U.S. §119(a) to Canadian Plant Breeder's Rights Application No. 14-8409, filed Jul. 31, 2014; the disclosure of which is incorporated herein by reference in its entirety.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventor in Raleigh, N.C., United States. One of the objectives of the breeding program was to develop a compact statured, reduced male and female fertility, semi-upright *Buddleja* with violet (RHS 83A) flowers. 'Miss Violet' was selected at a research station in Jackson Springs, N.C. in 2010 from a population of about 95 seedling progeny derived from a hand pollinated cross of 'Blue Chip'×'Miss Molly' made in summer 2009 in Raleigh, N.C. 'Blue Chip' was the female (seed) parent, and 'Miss Molly' was the male (pollen) parent in the aforementioned hybridization. 'Blue Chip' is a complex hybrid containing 3 different species and one botanical variety of *Buddleja* (*B. davidii, B. davidii* var. *nanhoensis, B.*

*lindleyana*, and *B. globosa*). 'Miss Molly' was derived from hybridization of 'Miss Ruby'×'Attraction'. 'Miss Ruby' was derived from hybridization of 'White Ball'×'Attraction'. 'White Ball' is a complex hybrid, presumably containing *B. davidii* and *B. fallowiana*. 'Attraction' was derived as an open-pollinated seedling of 'Honeycomb', which is a hybrid of *B. globosa*×*B. davidii*. NC2000-1 is a hybrid of 'Nanho Purple'×*Buddleja lindleyana*. 'Nanho Purple' is a variety derived from *Buddleja davidii* var. *nanhoensis*. All of the hybridizations described above, with the exception of the development of 'White Ball' and 'Attraction', were accomplished in the inventor's research program. The complete pedigree of 'Miss Violet' is shown in FIG. 4. Of all the parents used in the development of 'Miss Violet', the varieties 'Blue Chip' (U.S. Plant Pat. No. 19,991), 'Miss Molly' (U.S. Plant Pat. No. 23,425), 'Miss Ruby' (U.S. Plant Pat. No. 19,950), 'Attraction' (not patented), 'White Ball' (not patented), 'Nanho Purple' (not patented), and 'Honeycomb' (not patented), and the species *Buddleja lindleyana* are available in commerce.

The seeds resulting from the 2009 controlled hybridization process were harvested in fall of 2009 and germinated in a greenhouse in Raleigh, N.C. in the winter of 2010. The resulting 95 seedlings (approximate) were planted in field trials in spring of 2010 at a research station in Jackson Springs, N.C. These plants flowered in summer 2010, and one plant, designated NC2010-1, was selected in July, 2010 for its compact stature, semi-upright habit, attractive violet (RHS 83A colored flowers, oblong-elliptic leaves, non-functional male flower parts (anthers), and reduced seed set (reduced female fertility). This original plant demonstrated characteristics identical to those subsequently expressed on other plants when propagated from stem cuttings. This single plant is the subject of the present invention *Buddleja* 'Miss Violet'.

The inventor conducted the first asexual propagation of 'Miss Violet' in fall 2010 in Raleigh, N.C., and 'Miss Violet' has subsequently been propagated in the same location in years 2011 through 2013. In all cases, the original plant selection was propagated asexually by softwood to semi-hardwood stem cuttings. Such cuttings root readily under mist in about 14 to 21 days, and resume normal growth. Four plants derived from stem cuttings of the variety were established in experimental greenhouse trials in Raleigh, N.C. in fall, 2010 and in 2011. Subsequently, ten plants derived from stem cuttings were established in a field trial in Jackson Springs, N.C. in 2013. Through successive asexual propagations, the characteristics of the original plant have been maintained. Thus, plants derived from stem cuttings exhibit characteristics identical to those of the original plant, and no aberrant phenotypes have appeared.

Test plantings and performance evaluation over five years at a research station in Jackson Springs, N.C. and a greenhouse in Raleigh, N.C. demonstrate this variety to be relatively consistent in its characteristics even under the different growing conditions associated with yearly climatic variation.

Plants of the new variety are compact after establishment in the field, being less vigorous and more compact than most cultivars of butterfly bush available in commerce. Young plants have averaged about 62.0 cm of height growth per year. Plants are semi-upright in growth habit. Flowering occurs in the first year of growth on newly formed wood. The inflorescence is a panicle, and shows a deep violet flower color. Flowering usually begins in late May to early June in Jackson Springs, N.C., and continues throughout the growing season until the first freeze event in October or November. An individual inflorescence flowers for about 7-10 days, depending on temperature, but new flowers are made during the entire growing season. Flowers show reduced male and female fertility, and the new cultivar has set only limited seed in replicated field trials, an asset in landscape plantings.

'Miss Violet' is distinguished from other related known cultivars based on the unique combination of traits including compact plant size, dense semi-upright growth habit, green leaves (RHS N137C) with oblong-elliptic shape, attractive violet (RHS 83A) flower color, non-functional male flower parts (anthers), and reduced female fertility, resulting in low seed production. The cultural requirements for 'Miss Violet' are well-drained soil, full sun, and moderate moisture. 'Miss Violet' exhibits no serious pest or disease problems known to the inventors, except for occasional spider mite infestation during periods of hot, dry weather.

SUMMARY OF THE INVENTION

'Miss Violet' is a new and distinct variety of butterfly bush that has the following unique combination of desirable features outstanding in a new variety. In combination these traits set 'Miss Violet' apart from all other existing varieties of butterfly bush known to the inventors.

1. 'Miss Violet' has low vigor resulting in compact stature.
2. 'Miss Violet' is asexually propagated using softwood or semi-hardwood cuttings.
3. 'Miss Violet' demonstrates a dense, semi-upright growth habit.
4. 'Miss Violet' has female structures that show reduced fertility.
5. 'Miss Violet' has male structures (anthers) that are malformed and non-functional.
6. 'Miss Violet' has violet (RHS 83A) flower color.
7. 'Miss Violet' has oblong-elliptic leaf shape.

COMPARISON WITH KNOWN CULTIVARS

The closest comparisons known to the inventor are the varieties 'Miss Ruby' (U.S. Plant Pat. No. 19,950) and 'Miss Molly' (U.S. Plant Pat. No. 23,425). In direct comparisons of 'Miss Ruby' and 'Miss Molly' in the inventor's experimental trials, plants of 'Miss Violet' show violet (RHS 83A) flower color, compared to the red-purple (RHS 71B) flower color of 'Miss Ruby'. 'Miss Violet' also shows greater female sterility than 'Miss Ruby'. 'Miss Violet' flower color is distinctly different from the reddish-purple flower color of 'Miss Molly' (RHS 61B). 'Miss Violet' is male sterile (produces no anthers) and is highly female sterile, compared to the high male and female fertility of 'Miss Molly'.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'Miss Violet'. Photographs were taken from one-year-old plants growing in Jackson Springs, N.C.

DETAILED BOTANICAL DESCRIPTION OF THE VARIETY

The following is a detailed description of the botanical and ornamental characteristics of the subject butterfly bush 'Miss Violet'. Color data are based on *The Royal Horticultural Society Colour Chart*, The Royal Horticultural Society, London, 2007 edition. Where dimensions, sizes, colors and other characteristics are given, it is to be understood that such characteristics are approximations of averages set forth as accurately as practicable.

The descriptions reported herein are from two-year-old specimens grown in field research trials in Jackson Springs, N.C.

General information:

*Genus.*—*Buddleja.*

*Species.*—Complex hybrid, including *davidii, globosa*, and *lindleyana.*

*Denomination.*—'Miss Violet'.

*Commercial classification.*—Shrub, deciduous.

*Common name.*—Butterfly bush.

*Uses.*—Patio container plant, herbaceous perennial border, or shrub border for residential and commercial landscapes.

*Cultural requirements.*—Full sun exposure, well-drained soil, and moderate moisture.

Figure 1:
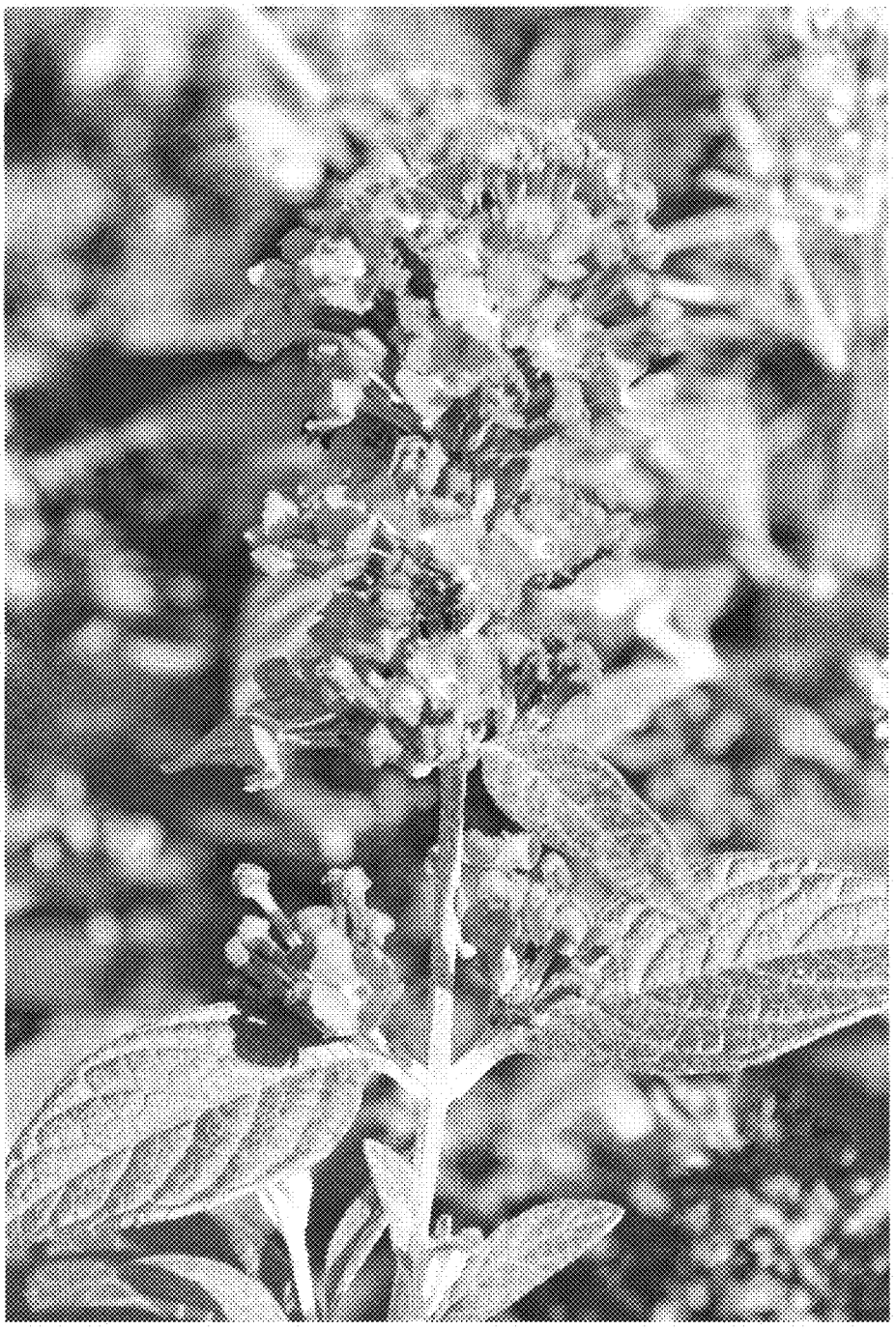
FIG. 1 shows the entire inflorescence of 'Miss Violet'.
Figure 2:
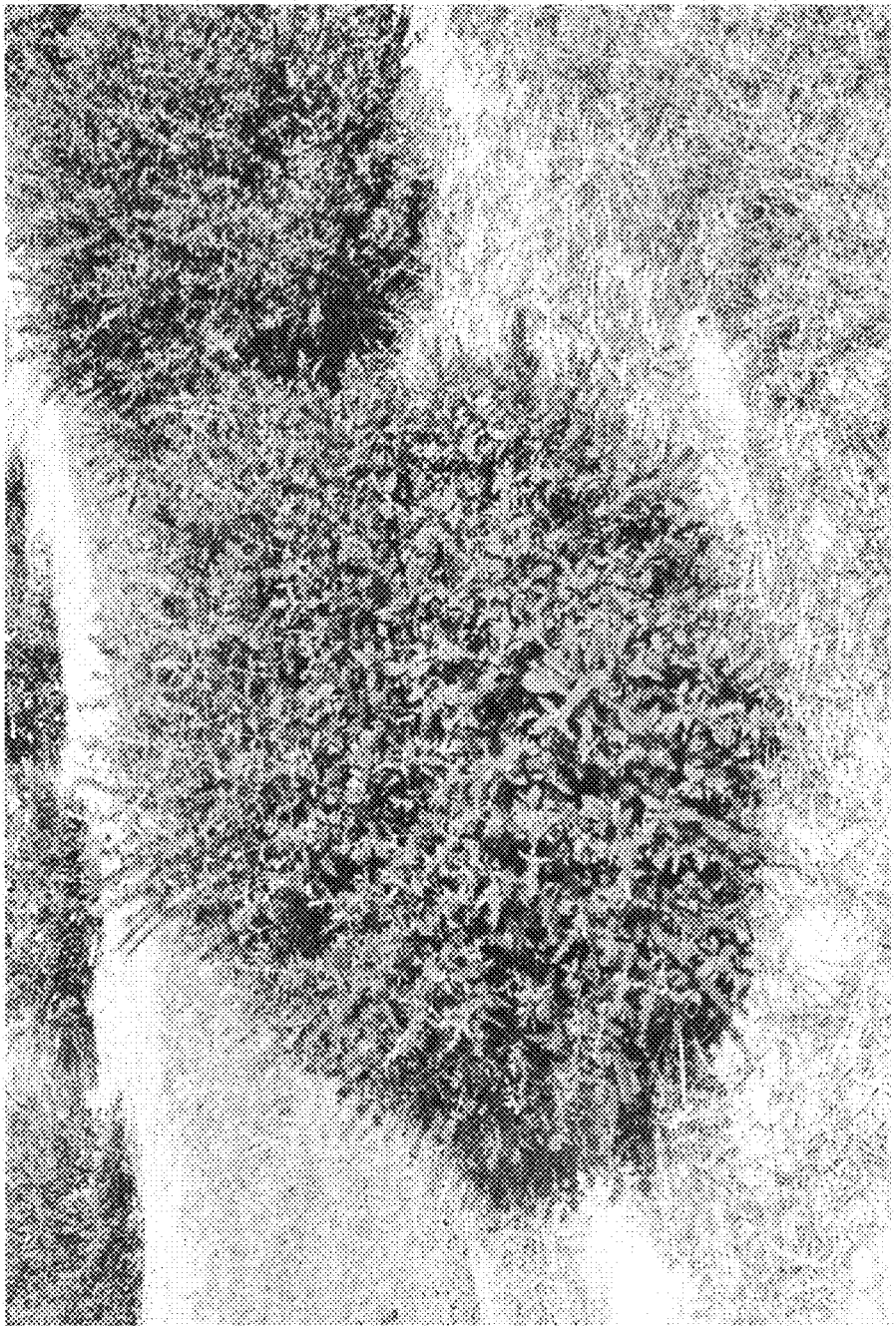
FIG. 2 shows a typical plant of 'Miss Violet', showing the compact stature, semi-upright growth habit, dense foliage, and violet flowers.
Figure 3:
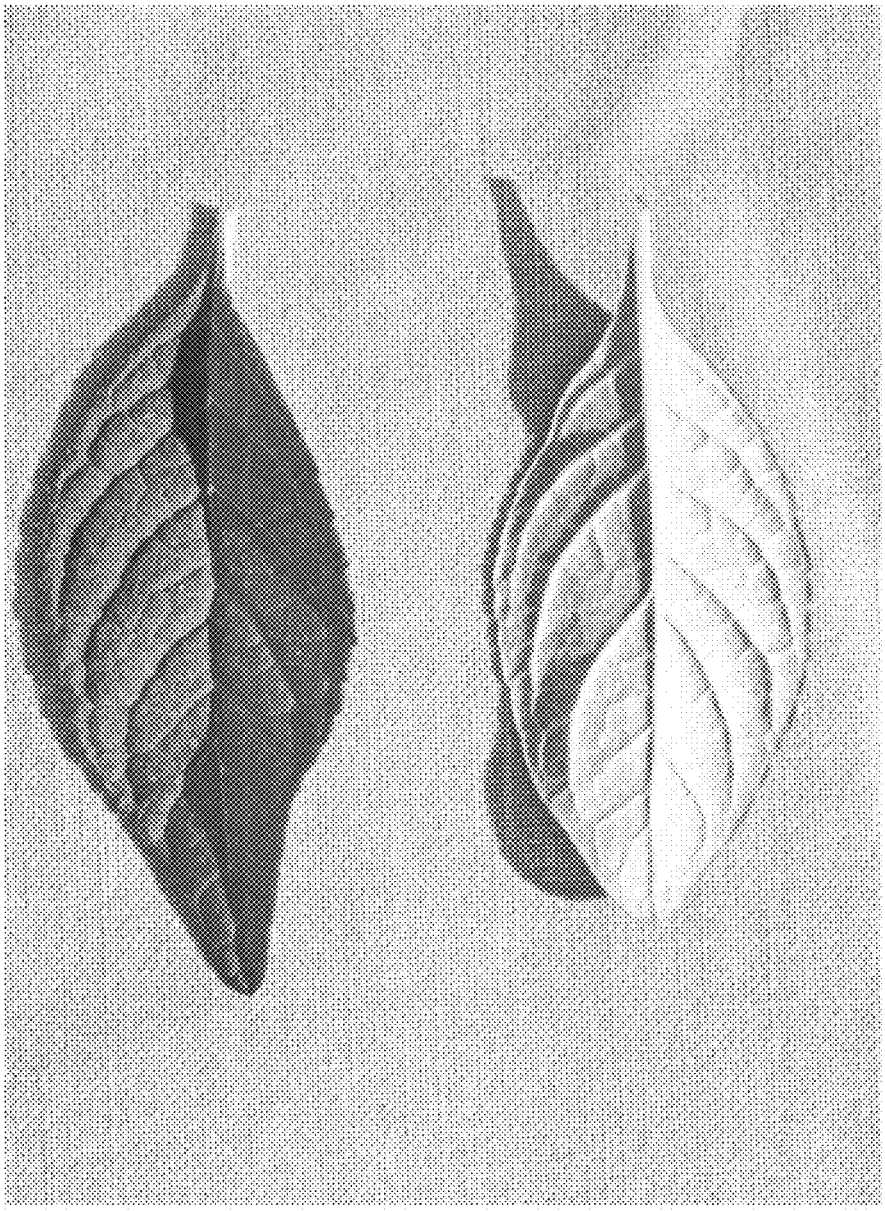
FIG. 3 shows the typical coloration and form of leaves of 'Miss Violet'. This figure shows the upper (top) and lower (bottom) leaf surface.
Figure 4:
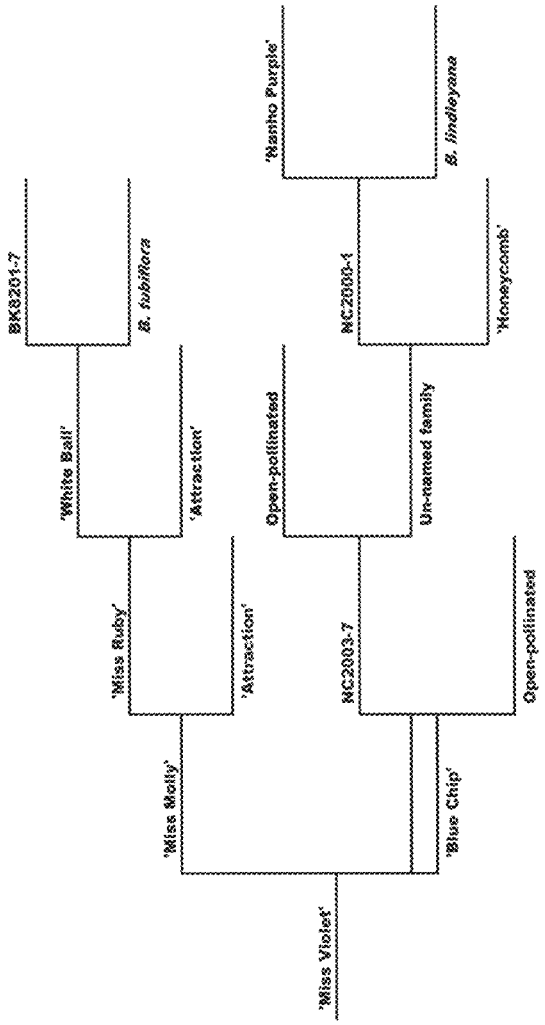
FIG. 4 provides the pedigree of *Buddleja* 'Miss Violet'

*Parentage*.—'Miss Violet' is a sixth-generation hybrid that resulted from the most recent cross pollination of 'Blue Chip'×'Miss Molly'. See FIG. 4 for entire pedigree.

The new variety is similar to the parent variety 'Blue Chip' in most horticultural characteristics, however the new variety differs in the following:

1. The new variety flower color is Violet 83A, flower color of 'Blue Chip' is Violet-Blue 90A.
2. Height of a 2 year old plant of the new variety is approximately 140 cm, height of a similar age plant of 'Blue Chip' is 46 cm.

The new variety is similar to the parent variety 'Miss Molly' in most horticultural characteristics, however the new variety differs in the following:

1. The new variety flower color is Violet 83A, flower color of 'Miss Molly' is Red-Purple 61B.
2. Height of a 2 year old plant of the new variety is approximately 140 cm, height of a similar age plant of 'Miss Molly' is 83 cm.

Plant description:

*Blooming period*.—June through October.
*Blooming habit*.—Paniculate.
*Vigor*.—Moderate vigor.
*Plant habit*.—Compact, semi-upright habit.
*Height and spread*.—1.2 m (height) and 1.6 m (width) on two-year-old unpruned plants.
*Hardiness*.—To date, hardy to minus 14 degrees Centigrade (7 degrees Fahrenheit). Not tested below this temperature. Anticipated adapted to USDA hardiness zones 5-9.
*Propagation*.—Softwood to semi-hardwood cuttings under intermittent mist. Roots typically form in 2-3 weeks.
*Root system*.—Fibrous, spreading.
*Seasonal interest*.—Violet (RHS 83A) flowers in spring, summer, and fall on a compact shrub with semi-upright growth habit.
*Disease and pest susceptibility and resistance*.—No particular susceptibility or resistance, except occasionally susceptible to spider mites under very hot and dry conditions.
*Special growing requirements*.—Moderate yearly pruning in late winter or early spring prior to bud break is recommended to encourage more profuse flowering.

Stems:

*Shape*.—Stem cross section is round.
*Length*.—Average 61.9 cm in one year of growth.
*Color*.—Yellow-green (RHS 145B) on recently formed shoots.
*Diameter*.—4.1 mm at base of new growth.
*Stem surface*.—Slight pubescence.
*Pubescence*.—Sparse.
*Internode length*.—5.9 cm in the middle of new growth.

Foliage:

*Type*.—Deciduous.
*Leaf arrangement*.—Opposite, decussate.
*Leaf division*.—Simple.
*Leaf shape*.—Oblong-elliptic.
*Leaf base*.—Attenuate.
*Leaf apex*.—Acute.
*Leaf venation*.—Pinnate.
*Leaf surface* (*abaxial*).—Slightly pubescent.
*Leaf margin*.—Serrulate.
*Leaf attachment*.—Petiolate.
*Petiole dimensions*.—9.2 mm length. 1 mm width.
*Petiole shape*.—Sulcate and slightly pubescent.
*Petiole color*.—Yellow-green (RHS 146C).
*Leaf color*.—Adaxial side: green (RHS N137C). Abaxial side: grayed-green (RHS 191B).
*Leaf midrib color*.—Abaxial side: greyed-green (RHS 194C).
*Leaf length*.—Avg. 8.9 cm.
*Leaf width*.—Avg. 3.6 cm.
*Foliar fragrance*.—None detectable.

Flowers:

*Inflorescence*.—Dense panicle, terminal and axillary.
*Flower shape*.—Salverform.
*Petals*.—4 in number.
*Fused or unfused*.—Fused at base.
*Petal margin*.—Entire.
*Petal apex*.—Rounded lobes, serrulate.
*Petal base*.—Truncate.
*Petal surfaces*.—Lacking pubescence.
*Petal shape*.—Rotund.
*Petal dimensions*.—4.4 mm total length. 3.6 mm width at apex. 1 mm width at base.
*Petal color*.—Adaxial and abaxial surface (open flower): Violet (RHS 83A). Closed flower prior to opening: Violet (RHS 83A).
*Corolla tube color*.—Outside of corolla: Violet (RHS 83A).
*Corolla throat color*.—Inside of corolla: Yellow-orange (RHS 21D).
*Corolla tube surfaces* (*inner and outer surfaces*).—Pubescence lacking.
*Corolla tube shape*.—Tubular.
*Color of peduncle*.—Green (RHS 142B).
*Peduncle surface*.—Glaucous.
*Peduncle length*.—18.0 cm.
*Peduncle shape*.—Flattened oval in cross section.
*Pedicel dimensions*.—2.0 mm in length and less than 1 mm in diameter.
*Pedicel color*.—Green (RHS 142B).
*Pedicel shape*.—Flattened oval in cross section.
*Pedicel surface*.—Glaucous.
*Flowers persistent or self-cleaning*.—Flowers are persistent.
*Lastingness of the overall inflorescence*.—7-10 days.
*Lastingness of an individual flower*.—3-5 days.
*Dimensions of inflorescence*.—18.0 cm length. 2.1 cm base width/tapering to 0.5 cm at tip.
*Quantity of flowers*.—Avg. 411.2 flowers per panicle (average of 5 panicles).
*Bud apex*.—Rounded lobes, serrulate.
*Bud surface*.—Glaucous. Lacking pubescence.
*Bud shape*.—Elongated, linear balloon.
*Calyx shape*.—Tubular.
*Calyx dimensions*.—1 mm in width and 3.4 mm in length.
*Sepals*.—Four in number.
*Sepal shape*.—Lanceolate.
*Sepal apex*.—Acute.
*Sepal margin*.—Entire.
*Sepal surface*.—Glabrous.
*Sepal color*.—Green (RHS 138D).
*Flower fragrance*.—Distinct sweet fragrance.

Reproductive organs:

*Stamens*.—Malformed and non-functional.

*Anther shape*.—Malformed.
*Filament size*.—Absent.
*Pollen amount*.—Absent.
*Pistil*.—One in number.
*Pistil dimensions*.—3 mm in length, and less than 1 mm in diameter.
*Stigma color*.—Yellow-green (RHS 144A).
*Style color*.—Yellow-green (RHS 144D).
*Ovary*.—Present.
*Ovary position*.—Superior.
*Ovary shape*.—Oval.
*Fertility*.—Essentially male (pollen) and female (seed) sterile.

OTHER CHARACTERISTICS

Fruit:

*Type*.—Capsule. Rarely observed. Reduced female fertility.
*Dimensions*.—2 mm length and 1 mm width.
*Color*.—Yellow-green (RHS 144C) when immature.

What is claimed is:

1. A new and distinct cultivar of *Buddleja* plant named 'Miss Violet' as illustrated and described herein.

* * * * *

Pedigree of *Buddleja* 'Miss Violet' (NC2010-1).